US008364499B2

(12) United States Patent
Maughan et al.

(10) Patent No.: US 8,364,499 B2
(45) Date of Patent: Jan. 29, 2013

(54) MEDICAL INFORMATION VALIDATION SYSTEM

(75) Inventors: Rex Wendell Maughan, Murray, UT (US); Jeffrey D. Lee, Grantsville, UT (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1792 days.

(21) Appl. No.: 11/551,283

(22) Filed: Oct. 20, 2006

(65) Prior Publication Data

US 2007/0112858 A1 May 17, 2007

Related U.S. Application Data

(66) Substitute for application No. 60/736,417, filed on Nov. 14, 2005.

(51) Int. Cl.
*G06Q 50/00* (2006.01)
(52) U.S. Cl. ................................. 705/2; 705/3
(58) Field of Classification Search ............. 705/2, 3
See application file for complete search history.

(56) References Cited

U.S. PATENT DOCUMENTS

| | | | |
|---|---|---|---|
| 7,158,890 B2 * | 1/2007 | Brumbach et al. ............. 702/19 |
| 2003/0049260 A1 * | 3/2003 | Bell ........................ 424/146.1 |
| 2004/0030578 A1 * | 2/2004 | Cross et al. .................... 705/2 |
| 2004/0152056 A1 | 8/2004 | Lamb et al. |
| 2004/0204910 A1 * | 10/2004 | Brumbach et al. ........... 702/185 |
| 2005/0154562 A1 | 7/2005 | Matsuura et al. |
| 2005/0251051 A1 | 11/2005 | Pougatchev et al. |
| 2005/0251424 A1 | 11/2005 | Sanders et al. |
| 2006/0036619 A1 | 2/2006 | Fuerst et al. |

* cited by examiner

*Primary Examiner* — Gerald J. O'Connor
*Assistant Examiner* — Neha Patel
(74) *Attorney, Agent, or Firm* — Alexander J Burke

(57) ABSTRACT

A system uses clinical data to help identify incorrect demographic information (such as gender or age) of a patient that may cause an erroneous critical or abnormal indication in medical tests and uses results of a clinical test to indicate possible demographic errors and various methods to modify a workflow to incorporate alternative tasks or to request verification of specific demographic facts. A system for validating patient medical information includes an input processor for receiving a laboratory test result value of a particular patient. A data processor automatically compares the received laboratory test result value with a predetermined normal value range for a patient having demographic characteristics of the particular patient, and compares the received laboratory test result value with a predetermined normal value range for a patient having different demographic characteristics than the particular patient. A communication processor initiates generation of an indication to a user indicating stored demographic information of the particular patient may be inaccurate.

15 Claims, 4 Drawing Sheets

FIGURE 3

Females:
Premature (26-28 weeks): 5-16 ng/dL
Premature (31-35 weeks): 5-22 ng/dL
Newborn: 20-64 ng/dL
1-7 months: Levels decrease during the first month to less than 10 ng/dL and remain at this level until puberty.
7-9 years: 1-12 ng/dL
10-11 years: 2-35 ng/dL
12-13 years: 5-53 ng/dL
14-15 years: 8-41 ng/dL
16-17 years: 8-53 ng/dL
Premenopausal: 10-54 ng/dL
Postmenopausal: 7-40 ng/dL

Males:
Premature (26-28 w): 59-125 ng/dL
Premature (31-35 w): 37-198 ng/dL
Newborn: 75-400 ng/dL
1-7 months: Levels decrease rapidly the first week to 20-50 ng/dL, and then increase to 60-400 ng/dL between 20-60 days. Levels then decline to prepubertal range levels of 3-10 ng/dL by seven months.
7-9 years: 0-8 ng/dL
10-11 years: 1-48 ng/dL
12-13 years: 5-619 ng/dL
14-15 years: 27-487 ng/dL
16-17 years: 154-738 ng/dL
18-39 years: 400-1080 ng/dL
40-59 years: 350-890 ng/dL
60 years and older: 350-720 ng/dL

MEDICAL INFORMATION VALIDATION SYSTEM

CROSS-REFERENCE TO RELATED APPLICATIONS

The present application is a non-provisional application of provisional application having Ser. No. 60/736,417 by R. W. Maughan et al. on Nov. 14, 2005.

FIELD OF THE INVENTION

The present invention concerns a system for validating patient medical information such as demographic information and laboratory test results and initiating review and corrective actions in response to validation.

BACKGROUND OF THE INVENTION

A number of the medical (e.g., laboratory) tests performed in patient diagnosis and treatment require correct demographic information in order to determine that a result is within a correct normal range or critical range as well as a type of test to be performed. Existing systems provide limited capability for ensuring patient demographic information is correct and typically rely on the demographic information obtained during a patient admission process. If patient demographic information is incorrect upon acquisition or is entered incorrectly, clinical tests that use the demographic information, or are reliant on the information, may produce erroneous result values. Consequently, erroneous normal, abnormal and/or critical ranges and results may be reported. The erroneous normal, abnormal and/or critical ranges or results that may be generated using incorrect demographic information may produce incorrect clinical decisions resulting in patient harm, indicate expensive and unnecessary treatment options and may cause unneeded patient concern.

Although a physician may know normal ranges for a particular test and can determine that the ranges are in error in a corresponding particular test result, the large number of tests that are used by an individual physician make this an almost impossible task for the physician. An individual physician is typically capable of remembering a small number of normal ranges. Consequently reliance on human memory risks error and unreliability. A system according to invention principles addresses this deficiency and related problems.

SUMMARY OF THE INVENTION

A system uses clinical data to help identify incorrect demographic information (such as gender or ate) of a patient that may cause an erroneous critical or abnormal indication in medical tests and modifies a workflow (worker or device task sequence) to incorporate alternative tasks or to request verification of specific demographic facts. A system for validating patient medical information includes an input processor for receiving a laboratory test result value of a particular patient. A data processor automatically compares the received laboratory test result value with a predetermined normal value range for a patient having demographic characteristics of the particular patient, and compares the received laboratory test result value with a predetermined normal value range for a patient having different demographic characteristics than the particular patient. A communication processor initiates generation of an indication to a user indicating stored demographic information of the particular patient may be inaccurate.

BRIEF DESCRIPTION OF THE DRAWINGS

FIG. 3 illustrates normal values for males and females for total serum testosterone, in accordance with invention principles.

DETAILED DESCRIPTION OF THE INVENTION

Figure 1:
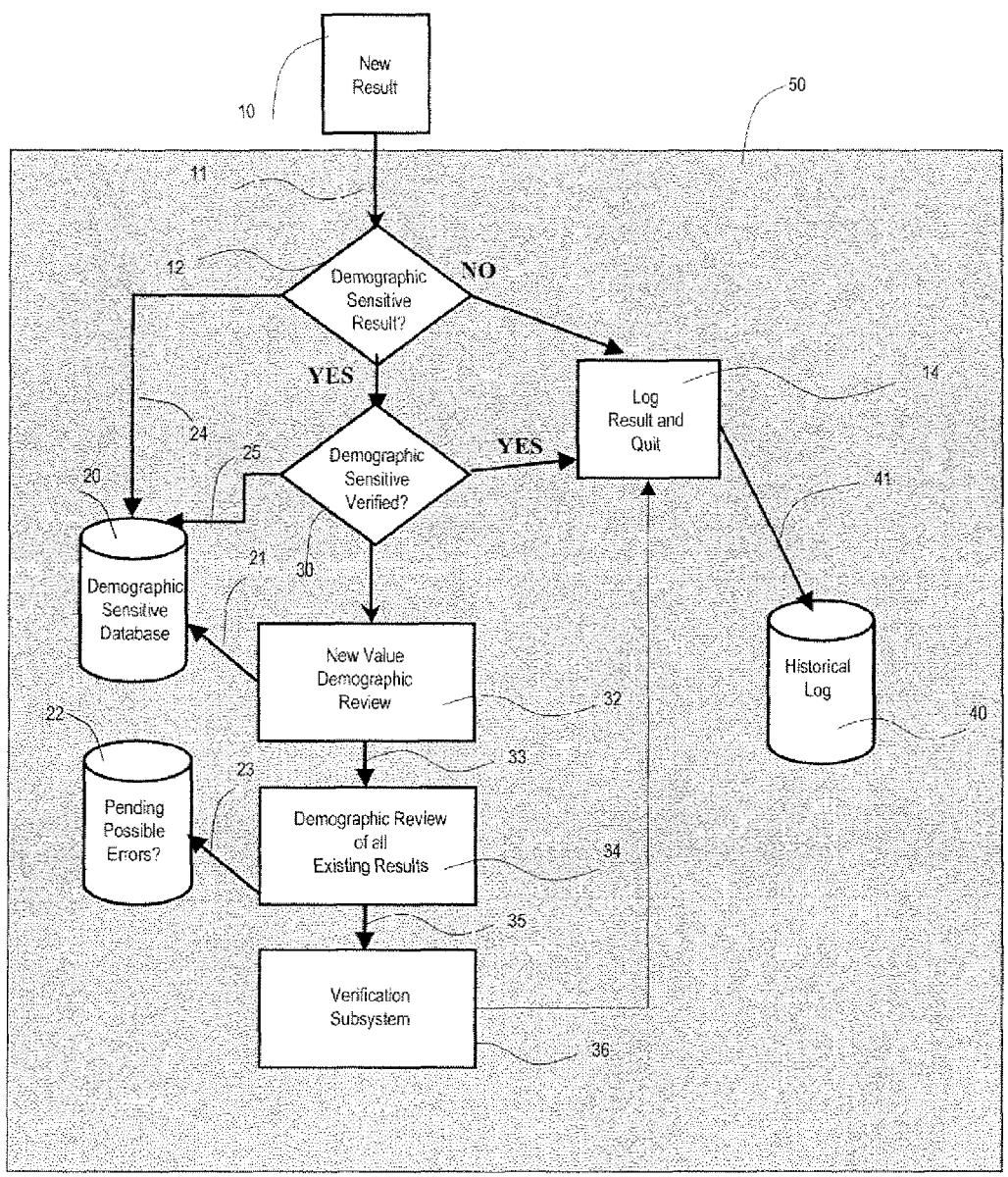
FIG. 1 shows a system for processing patient medical result data and validating patient medical information, in accordance with invention principles.

A system according to invention principles uses results of patient clinical and laboratory tests to modify a workflow to initiate (or request) a verification of a specific item of demographic information. In response to a request for verification of a specific item of demographic information, the system performs multiple activities. The system prompts a user viewing a patient medical result via a user interface display image menu to verify a specific item of demographic information such as gender. The system also places a request on a clinician (e.g. a nurse) electronic worklist (a list of tasks to be performed) or inbox, to verify a specific item of demographic information. Printed reports showing demographic information that needs to be verified are provided by the system for use by a ward clerk, admitting clerk or other medical support personnel. The system also automatically initiates sending of a faxed report to a physician or outpatient clinic office requesting verification of demographic information. In a hospital, or other healthcare provider organization, insurance information is often collected and verified during admission. The system validates the demographic information to ensure record accuracy. This is done in response to a request to a billing office to verify demographic information obtained from an insurance carrier, for example. The system further initiates a request to an electronic clearing house (an intermediary organization for processing insurance claims from healthcare providers for submission to payer organizations) for demographic information verification using information acquired and stored from previous claims or insurance inquiries.

In response to verification by the system that demographic information is incorrect, a user is prompted to correct an erroneous demographic value via a user interface. Also a request is communicated to a physicians inbox or worklist to suggest that tests which are subject to demographic normal differences either be retested or the normal ranges adjusted with an appropriate historical record retained.

A workflow is a task sequence performed by a device, worker or combination of both. An executable application as used herein comprises code or machine readable instruction for implementing predetermined functions including those of an operating system, healthcare information system or other information processing system, for example, in response user command or input. An executable procedure is a segment of code (machine readable instruction), sub-routine, or other distinct section of code or portion of an executable application for performing one or more particular processes and may include performing operations on received input parameters (or in response to received input parameters) and provide resulting output parameters. A processor as used herein is a device and/or set of machine-readable instructions for performing tasks. A processor comprises any one or combination of, hardware, firmware, and/or software. A processor acts upon information by manipulating, analyzing, modifying, converting or transmitting information for use by an executable procedure or an information device, and/or by routing the information to an output device. A processor may use or comprise the capabilities of a controller or microprocessor, for example. A display processor or generator is a known element comprising electronic circuitry or software or a combination of both for generating display images or portions thereof. A user interface comprises one or more display images enabling user interaction with a processor or other device.

FIG. 1 shows a system for processing patient medical result data and validating patient medical information. In response to receiving a new medical result (e.g., a laboratory test result) 10 from either an internal executable application or through an interface to an external system, a Demographic Result System (DRS) 50 is activated through interface 11. The new medical result parameter type is compared with data in database 20 identifying those medical result types that are sensitive to, and variable with, demographic information and is accessed via interface 24. In response to the determination that the new medical result 10 is demographically sensitive (step 12), system 50 determines (step 30) if the demographic result has already been verified. If the new medical result 10 is determined to not be demographically sensitive (step 12) then system 50 stores (step 14) the medical result 10 and data indicating time and date of receipt and exits. System 50 further outputs an audit record, indicating the data transfer, access and updates that have occurred, to historical log store 40 through interface 41 and completes processing.

If new medical result 10 is determined (step 12) to be demographically sensitive information and has already been verified (step 30) as correct, system 50 via interface 15 stores new medical result 10 and exits (step 14) and system 50 outputs an audit record as previously described. If new medical result 10 is determined 12 to be demographically sensitive information and but has not already been verified (step 30) to be correct, system 50 performs New Value Demographic Review function 32. The New Value Demographic Review function 32 uses database 20 to determine if medical result 10 is within a normal range for a patient having the patient's demographic characteristics. The demographic characteristics comprise at least one of, (a) age, (b) gender, (c) height, (d) weight and (e) race, for example. If medical result 10 is outside of a normal range, result 10 is compared with predetermined, stored normal range values for result 10 for a patient of different gender and age ranges, for example. If the medical result 10 value falls within a normal range for a different gender or age range, medical result 10 together with data indicating the suspected demographic error and suspected correct age or gender is passed to Demographic Review function 34 of existing results through interface 33.

Existing value demographic Review function 34 evaluates individual existing results (excluding new result 10 and including all or a portion of existing medical results of a patient as selected by a user) and determines if a suspected demographic change, such as of age or gender, provides a more appropriate result range for existing medical results of the patient. Function 34 also determines whether the demographic change indicates each existing medical result is a critical or abnormal result for the patient. Existing medical results that have a different range based on the suspected values are stored into a Pending Possible Errors database 22 through interface 23. If a demographic review of existing results has been previously performed for the patient, the new result information adds to or modifies existing values in Pending Possible Errors database 22.

New and Existing Value Demographic Review functions 32 and 34 respectively, determine potential demographic information errors by comparing medical result data with normal, critical and abnormal result value ranges for a patient having various changed characteristics. The various characteristics include. Age, Sex, Female Postmenopausal Status, Female Premenopausal Status, Pregnancy Indicator, Vaccination completed (such as Diphtheria, Tetanus, infuenza, and Measles). Functions 32 and 34 also determine potential demographic information errors based on various changed characteristics including, Menstrual Cycle (including Early follicular phase, Late follicular phase and Luteal phase), Gestational Age, Prepubertal Status, Diabetic or Nondiabetic Status and Race. A configuration processor and user interface enable an individual identified specific demographic information error to be assigned a probabilistic factor and an associated confidence threshold to enable filtering of potential errors by likelihood of error. A confidence threshold value is selected to reduce requests for verification. For example, a confidence threshold may be set higher by requiring the combination of four possible errors for a probability factor to meet the threshold to indicate that a possible demographic error has occurred. Other users or organizations may set a confidence threshold and associated probability factor lower so that one possible error triggers demographic error processing, for example. Race is also a characteristic that may affect medical result data (e.g., laboratory test results). Sickle cell anemia, for example, is predominantly found in African-American patients in the USA. Similarly, a positive result for pregnancy may indicate a patient is female.

In response to a determination that a potential demographic error has occurred, the verification subsystem 36 is activated through interface 35. Verification subsystem 36 requests verification of the potential demographic error in the demographic information through at least one of a number of methods selected or pre-configured by a user, organization, facility, nursing unit or department. Verification subsystem 36 prompts a user viewing medical result 10 via a user interface to verify a specific item of demographic information such as gender. Verification subsystem 36 also communicates message data representing a request for addition of a task to an electronic worklist or inbox of tasks for performance by a clinician, such as a nurse, e.g., to verify a specific item of demographic information. The worklist request includes a suggested demographic information value change to correct an identified error such as to provide proper gender or age information which a clinician can verify. In response to a clinician verifying a suggested demographic information value, system 36 updates the demographic information of the patient.

Verification subsystem 36 further provides printed reports showing demographic information that needs to be verified showing current demographic item or status value and a suggested new value for use by a ward clerk, admitting clerk or other medical support personnel. In addition verification subsystem 36 initiates communication by facsimile transmission or other method of a report to a physician or outpatient clinic office requesting verification of demographic information. Similarly, subsystem 36 initiates communication of a request to a billing office to verify demographic information obtained from an insurance carrier. Insurance information including demographic information is collected and verified during admission and demographic information is often available for use in verification by a clinician. A request to an electronic clearing house for demographic information verification using information stored from previous claims or insurance inquiries is also initiated by subsystem 36. In response to verification actions being performed by verification subsystem 36, system 36 stores (step 14) verification action results and data indicating time and date of receipt of the verification action results and exits. Further, data indicating the verification actions performed is stored in historical log 40 through interface 41 and processing completes.

Figure 2:
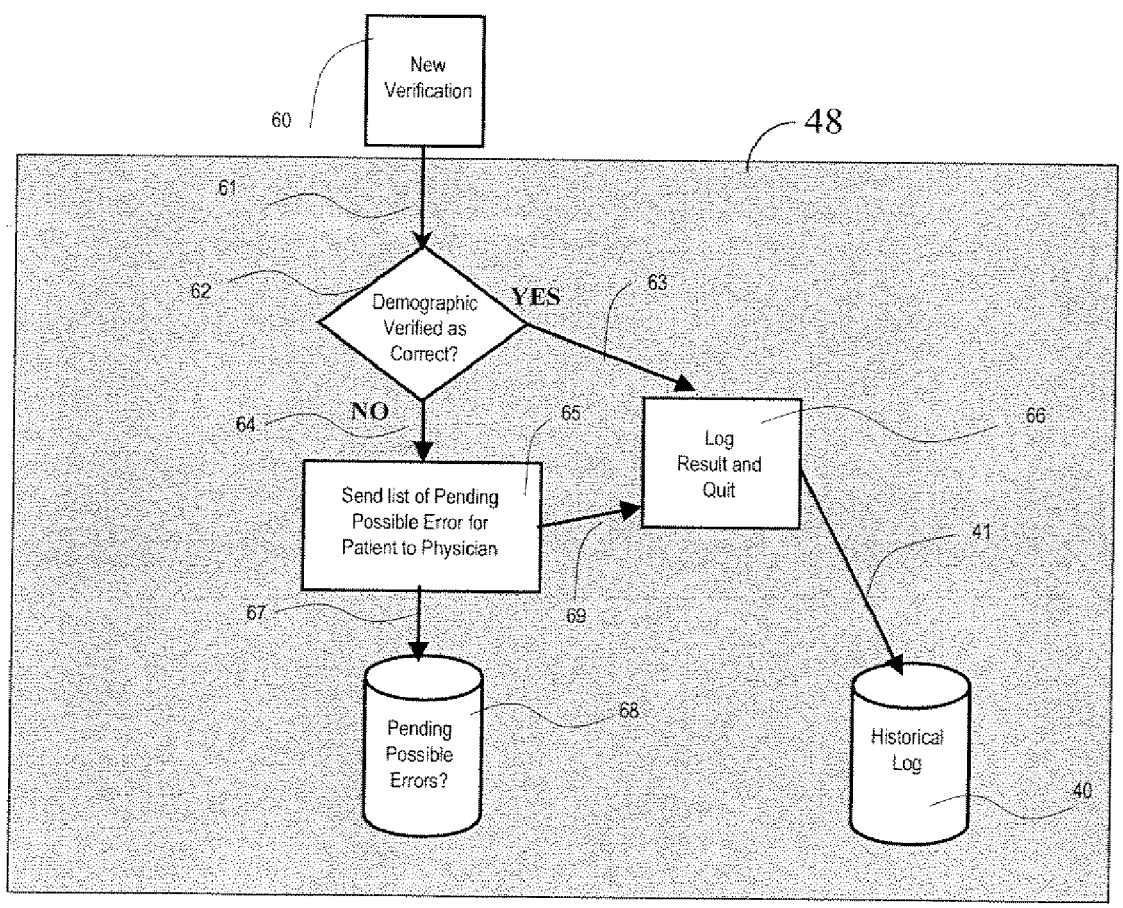
FIG. 2 shows a user interactive process for validating patient medical information, in accordance with invention principles.

FIG. 2 shows a user interactive process for validating patient medical information. When data 60 for verification is received from verification subsystem 36, the Verification function 48 is activated via interface 61. If verification function 48 determines that the demographic information is correct (step 62), function 48 stores medical Result 10 (step 66) via interface 63 and records the result of the verification in historical log 40 through interface 41 before ending processing. If verification function 48 determines the demographic information is incorrect (step 62), the process proceeds to step 65 through interface 64. Function 48 in step 65 prepares a list of pending possible errors and stores information representing the errors in database 68 through interface 67. Verification function 48 communicates a list of possible errors to a physician and a message requesting associated action by the physician. In response, the physician receives an item in an inbox with a notification that a specific piece of demographic information is incorrect. The physician also receives a list of tests that show incorrect value ranges and corresponding correct ranges for medical result 10 and other results based on changed demographic information. For tests that are inappropriate for the corrected demographic information, the physician is given an opportunity to order the proper test by the system which provides data representing appropriate candidate tests in a user interface display image. Data identifying actions taken by function 48 in step 65 is recorded in historical log 40 through interfaces 69 and 41 (step 66).

In an example of system operation, a Serum Total Testosterone test is a laboratory test that may produce an abnormal indicator if gender is not reported correctly. FIG. 3 illustrates normal values for males and females for total serum testosterone. Consequently, if a 39-year-old male tested with a total serum testosterone level of 1000 ng/dl was incorrectly listed as a female, the result would show as a critical value showing that the result exceeds the maximum value by approximately 946 ng/dl or exceeds the normal range by more than 1,800%. Further, many laboratories and clinicians send laboratory test results directly to a patient which may cause unnecessary concern and worry for the patient for a result that may in fact be normal. Some tests, such as some testosterone level test should be restricted to being performed on one render since the accuracy of the test is not sufficient to be used with the other gender. For example, some female testosterone testing methods have better accuracy for the female lower normal levels and should be used instead of the male testing methods. A male test method would produce a more inaccurate result if it is used on a blood sample from a female. Therefore incorrect gender information may trigger reporting of a laboratory test result that has both an incorrect normal range and is out of context for the gender of the patient.

The system advantageously automatically uses test result values to request demographic information verification in response to automatically determining that a test result value would be normal for a patient having different demographic information, such as gender, than the information currently on record. The verification in response to determination of potentially incorrect demographic information prevents incorrect test result ranges with associated critical flagging indicators from erroneously being used in clinical decision making. This provides safer and lower cost health care delivery for patients.

Figure 4:
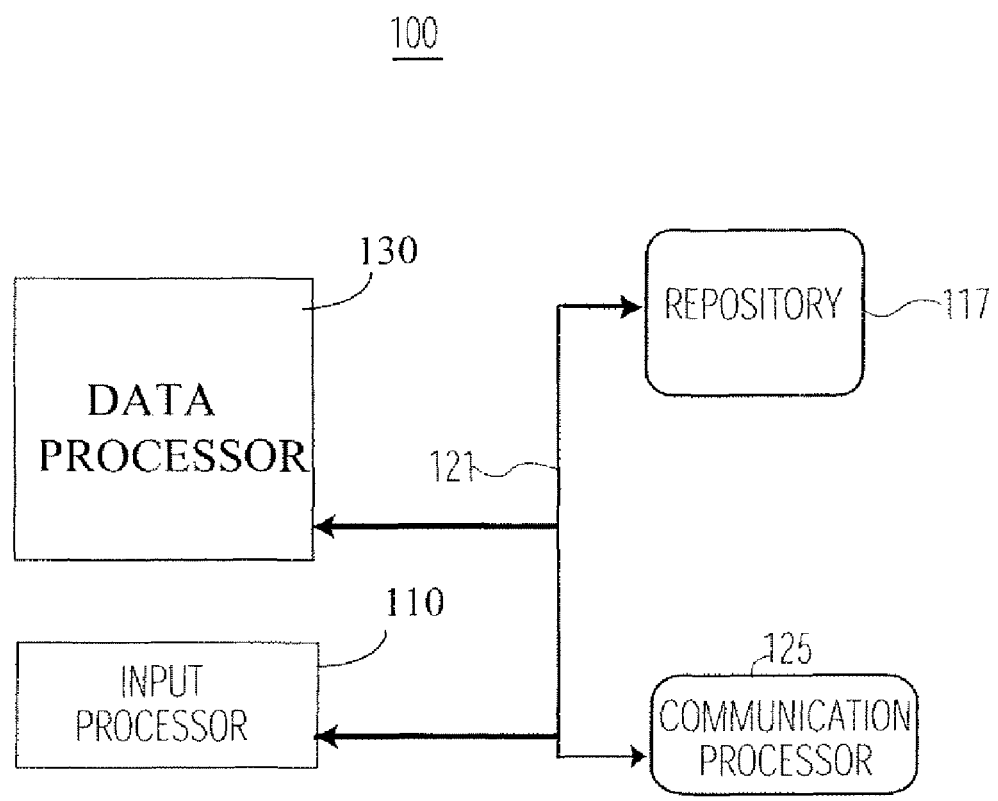
FIG. 4 shows a system for validating patient medical information in accordance with invention principles.

FIG. 4 shows system 100 for validating patient medical information comprising input processor 110, at least one repository 117, data processor 130 and communication processor 125 (including a video and/or audio reproduction device such as a display, speaker etc.) bi-directionally intercommunicating using communication path 121. The communication path 121 (otherwise called network, bus, link, connection, channel, etc.) may use any type of protocol or data format. The protocol or data format includes, but is not limited to, one or more of the following: an Internet Protocol (IP), a Transmission Control Protocol Internet Protocol (TCP/IP), a Hyper Text Transmission Protocol (HTTP), an RS232 protocol, an Ethernet protocol, a Medical Interface Bus (MIB) compatible protocol, a Local Area Network (LAN) protocol, a Wide Area Network (WAN) protocol, a Campus Area Network (CAN) protocol, a Metropolitan Area Network (MAN) protocol, a Home Area Network (HAN) protocol, an Institute Of Electrical And Electronic Engineers (IEEE) bus compatible protocol, a Digital and Imaging Communications (DICOM) protocol, and a Health Level Seven (HL7) protocol.

Input processor 110 receives a laboratory test result value of a particular patient from a laboratory information system and stores the received laboratory test result value in at least one repository 117 together with previously acquired laboratory test result values of the particular patient. Data processor 130 automatically compares the received laboratory test result value with a predetermined normal value range for a patient having demographic characteristics of the particular patient and in response to a determination the received laboratory test result value is outside of the predetermined normal value range, compares the received laboratory test result value with a predetermined normal value range for a patient having different demographic characteristics than the particular patient. The normal value range corresponds to different demographic characteristics selected in a predetermined order by firstly varying one of the demographic characteristics at a time and secondly varying multiple demographic characteristics. Data processor 130 further compares a value of the previously acquired laboratory test result values in repository 117 with a predetermined normal value range for a patient having different demographic characteristics than the particular patient. The demographic characteristics comprise at least one of, age, gender, height, weight, race and residential address.

In response to a comparison, communication processor 125 initiates generation of an indication to a user indicating stored demographic information of the particular patient may be inaccurate. Communication processor 125 initiates generation of indications to a user prompting the user to review an item of demographic information of the particular patient and suggesting alternative demographic information for the particular patient, e.g. via one or more display images presenting the indications to the user via a user interface within unit 130. Communication processor 125 also initiates generation of an item on a work task list of a healthcare worker for the worker to review an item of demographic information of the particular patient and also initiates generation and communication of a report indicating an item of demographic information of the particular patient to be reviewed. In addition, communication processor 125 initiates communication of a message to a destination application for initiating verification of a demographic characteristic of the particular patient.

The system and processes presented in FIGS. 1-4 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system according to invention principles is applicable anywhere that clinical data with normal, abnormal or critical ranges is used and demographic information is relevant to these ranges. Further, any of the functions provided in the systems of FIGS. 1, 2 and 4 may be implemented in hardware, software or a combination of both and may reside on one or more processing devices located at any location of a network linking the FIG. 4 elements or another linked network including another intra-net or the Internet.

What is claimed is:

1. A system for validating patient medical information, comprising:
   an input processor for receiving a laboratory test result value of a particular patient;
   a data processor for automatically,
      comparing the received laboratory test result value with a predetermined normal value range for a patient having demographic characteristics of said particular patient and,
      comparing said received laboratory test result value with a predetermined normal value range for a patient having different demographic characteristics than said particular patient; and
   a communication processor for, in response to the comparison with a predetermined normal value range for a patient having different demographic characteristics, initiating generation of an indication to a user indicating stored demographic information of said particular patient is potentially inaccurate.

2. A system according to claim 1, wherein
   said demographic characteristics comprise at least one of, (a) age, (b) gender, (c) height, (d) weight and (e) race.

3. A system according to claim 2, wherein
   said demographic characteristics comprise a residential address.

4. A system according to claim 2, wherein
   said data processor compares said received laboratory test result value with a predetermined normal value range for a patient having different demographic characteristics than said particular patient in a predetermined order.

5. A system according to claim 4, wherein
   said data processor compares said received laboratory test result value with a predetermined normal value range for a patient having different demographic characteristics in said predetermined order by firstly varying one of said demographic characteristics at a time and secondly varying multiple demographic characteristics.

6. A system according to claim 1, including
   a repository of previously acquired laboratory test result values of said particular patient and wherein, in response to a comparison,
   said data processor automatically compares a value of said previously acquired laboratory test result values with a predetermined normal value range for a patient having different demographic characteristics than said particular patient.

7. A system according to claim 1, wherein
   said communication processor initiates generation of a display image presenting said indication to said user.

8. A system for validating patient medical information, comprising:
   an input processor for receiving a laboratory test result value of a particular patient;
   a data processor for automatically,
      comparing the received laboratory test result value with a predetermined normal value range for a patient having demographic characteristics of said particular patient and in response to a determination said received laboratory test result value is outside of said predetermined normal value range,
      comparing said received laboratory test result value with a predetermined normal value range for a patient having different demographic characteristics than said particular patient; and
   a communication processor for, in response to said comparisons, initiating generation of an indication to a user indicating stored demographic information of said particular patient is potentially inaccurate.

9. A system according to claim 8, wherein
   said communication processor initiates generation of an indication to a user suggesting alternative demographic information for said particular patient.

10. A system according to claim 8, wherein
   said communication processor initiates generation of an indication to a user prompting said user to review an item of demographic information of said particular patient.

11. A system according to claim 8, wherein
   said communication processor initiates generation of an item on a work task list of a healthcare worker for said worker to review an item of demographic information of said particular patient.

12. A system according to claim 8, wherein
   said communication processor initiates generation and communication of a report indicating an item of demographic information of said particular patient to be reviewed.

13. A system according to claim 8, wherein
   said communication processor initiates communication of a message to a destination application for initiating verification of a demographic characteristic of said particular patient.

14. A system for validating patient medical information, comprising:
   an input processor for receiving a laboratory test result value of a particular patient;
   a repository of previously acquired laboratory test result values of said particular patient;
   a data processor for automatically,
      comparing the received laboratory test result value with a predetermined normal value range for a patient having demographic characteristics of said particular patient and in response to a determination said received laboratory test result value is outside of said predetermined normal value range,
      comparing said received laboratory test result value with a predetermined normal value range for a patient having different demographic characteristics than said particular patient and
      comparing a value of said previously acquired laboratory test result values with a predetermined normal value range for a patient having different demographic characteristics than said particular patient; and a communication processor for, in response to the comparison with a predetermined normal value range for a patient having different demographic characteristics, initiating generation of an indication to a user indicating stored demographic information of said particular patient is potentially inaccurate.

15. A system according to claim 14, wherein
said communication processor initiates generation of an indication to a user suggesting alternative demographic information for said particular patient.

* * * * *